(12) United States Patent
Haeberlein et al.

(10) Patent No.: US 10,653,594 B2
(45) Date of Patent: May 19, 2020

(54) METHODS AND KITS OF REMOVING CALCULUS

(71) Applicant: 3M INNOVATIVE PROPERTIES COMPANY, St. Paul, MN (US)

(72) Inventors: Ingo R. Haeberlein, Weilheim (DE); Evan Koon Lun Yuuji Hajime, Woodbury, MN (US); Petra L. Kohler Riedi, Minneapolis, MN (US); Chuntao Cao, Woodbury, MN (US); Joel D. Oxman, Minneapolis, MN (US); Steven P. Swanson, Blaine, MN (US); Rainer A. Guggenberger, Herrsching (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 15/535,556

(22) PCT Filed: Dec. 2, 2015

(86) PCT No.: PCT/US2015/063335
§ 371 (c)(1),
(2) Date: Jun. 13, 2017

(87) PCT Pub. No.: WO2016/099875
PCT Pub. Date: Jun. 23, 2016

(65) Prior Publication Data
US 2017/0367941 A1 Dec. 28, 2017

Related U.S. Application Data
(60) Provisional application No. 62/091,715, filed on Dec. 15, 2014.

(51) Int. Cl.
| | | |
|---|---|---|
| *A61K 8/22* | (2006.01) | |
| *A61K 8/38* | (2006.01) | |
| *A61K 8/66* | (2006.01) | |
| *A61Q 11/00* | (2006.01) | |
| *A61K 8/81* | (2006.01) | |
| *A61K 8/60* | (2006.01) | |

(52) U.S. Cl.
CPC ............ *A61K 8/22* (2013.01); *A61K 8/38* (2013.01); *A61K 8/60* (2013.01); *A61K 8/66* (2013.01); *A61K 8/8176* (2013.01); *A61Q 11/00* (2013.01); *A61K 2800/884* (2013.01)

(58) Field of Classification Search
CPC .................................. A61K 7/16; A61K 7/20
USPC ........................................................ 424/53
See application file for complete search history.

(56) References Cited

U.S. PATENT DOCUMENTS

| | | |
|---|---|---|
| 1,482,367 A | 1/1924 | Elledge |
| 3,372,125 A | 3/1968 | Hill |
| 3,535,421 A | 10/1970 | Briner |
| 3,678,154 A | 7/1972 | Widder |
| 4,155,868 A | 5/1979 | Kaplan |
| 4,381,247 A | 4/1983 | Nakagawa |
| 4,417,993 A | 11/1983 | Gergely |
| 4,522,805 A | 6/1985 | Gordon |
| 4,528,180 A * | 7/1985 | Schaeffer ............... A61K 8/042 222/192 |
| 4,894,220 A | 1/1990 | Nabi |
| 5,071,439 A | 12/1991 | Weible |
| 5,403,578 A | 4/1995 | Gordon |
| 5,670,138 A * | 9/1997 | Venema ............... A61K 8/0216 424/435 |
| 5,908,614 A | 6/1999 | Montgomery |
| 6,331,291 B1 | 12/2001 | Glace |
| 6,379,654 B1 | 4/2002 | Gebreselassie |
| 6,440,396 B1 | 8/2002 | McLaughlin |
| 6,485,709 B2 | 11/2002 | Banerjee |
| 6,669,929 B1 | 12/2003 | Boyd |
| 6,685,921 B2 | 2/2004 | Lawlor |
| 7,530,808 B2 | 5/2009 | Cao |
| 7,740,479 B2 | 6/2010 | Allred |
| 7,816,423 B2 | 10/2010 | Karim |
| 8,647,608 B2 | 2/2014 | Yang |
| 8,906,981 B2 | 12/2014 | Yang |
| 2002/0141949 A1 | 10/2002 | Banerjee |
| 2003/0194382 A1 | 10/2003 | Chang |
| 2004/0120900 A1 | 6/2004 | Arsenault |
| 2005/0118116 A1 | 6/2005 | Pons Biescas |
| 2005/0196348 A1 | 9/2005 | Georgiades |
| 2006/0051385 A1 | 3/2006 | Scholz |

(Continued)

FOREIGN PATENT DOCUMENTS

| | | |
|---|---|---|
| CN | 104173197 | 12/2014 |
| DE | 1944308 | 3/1971 |

(Continued)

OTHER PUBLICATIONS

Kraus et al., "Salivary Catalase and Peroxidase values in Normal Subjects and in Persons with Periodontal Disease." O.S, O.M, & O.P. Jan. 1958; vol. 11 No. 1; p. 95-102 (Year: 1958).*
Home Remedies, "Get Rid of Plaque & Tartar on Teeth with Natural Remedies." HomeRemedies.com, Oct. 30, 2009; 3 pages. (Year: 2009).*
Putt et al., "Custom Tray Application of Peroxide Gel as an Adjunct to Scaling and Root Planing in the Treatment of Periodontitis: Results of a Randomized Controlled Trial after Six Months." J Clin Dent 2013;24:100-107 (Year: 2013).*
Easton, "The Behaviour of Mixtures of Hydrogen Peroxide and Water. Part 1—Determination of the Densities of Mixtures of Hydrogen Peroxide and Water", Transactions of the Faraday Society, 1952, vol. 48, pp. 796-801.

(Continued)

*Primary Examiner* — Walter E Webb
(74) *Attorney, Agent, or Firm* — 3M IPC

(57) ABSTRACT

Methods and kits for removing calculus from a tooth. The method includes applying a component A comprising hydrogen peroxide or a precursor thereto to the tooth; applying a component B comprising a catalase to the tooth, thereby generating oxygen; and removing at least a part of the calculus from the tooth; wherein the component A is applied before or after the component B is applied.

23 Claims, 1 Drawing Sheet

(56) References Cited

U.S. PATENT DOCUMENTS

| | | |
|---|---|---|
| 2006/0099155 A1 | 5/2006 | MacDonald |
| 2006/0198803 A1 | 9/2006 | Giniger |
| 2009/0220919 A1 | 9/2009 | Yang |
| 2011/0305738 A1 | 12/2011 | Ladizinsky |
| 2012/0282234 A1 | 11/2012 | Min |
| 2017/0367941 A1 | 12/2017 | Haeberlein |
| 2019/0231649 A1 | 8/2019 | Kohler Riedi et al. |

FOREIGN PATENT DOCUMENTS

| | | |
|---|---|---|
| FR | 2787778 | 6/2000 |
| GB | 1492660 | 11/1977 |
| JP | 0597640 | 4/1993 |
| RU | 2432620 | 10/2011 |
| WO | WO 1992-07550 | 5/1992 |
| WO | 1998-43603 | 10/1998 |
| WO | 1998-057653 | 12/1998 |
| WO | 2009-109533 | 9/2009 |
| WO | WO 2012-072777 | 6/2012 |
| WO | 2013-055478 | 4/2013 |
| WO | WO 2013-055478 | 4/2013 |
| WO | 2015-073246 | 5/2015 |
| WO | 2016-099875 | 6/2016 |
| WO | 2017/223161 | 12/2017 |
| WO | 2018-075149 | 4/2018 |
| WO | 2018-075150 | 4/2018 |

OTHER PUBLICATIONS

International Search Report for PCT International Application No. PCT/US2015/063335, dated Mar. 10, 2016, 6 pages.
U.S. Appl. No. 16/305,107, filed Nov. 28, 2018.
International Application No. PCT/US2017/075149, filed Sep. 5, 2017, which claims the benefit of U.S. Appl. No. 62/410,706, filed Oct. 20, 2016.
International Application No. PCT/US2017/050056, filed Sep. 5, 2017, which claims the benefit of U.S. Appl. No. 62/410,711, filed Oct. 20, 2016.
"Iodide", Wikipedia, [retrieved from the internet on Jun. 12, 2019], URL <https://en.wikipedia.org/wiki/Iodide>, pp. 1-4.
Bray, "Reactions Involving Hydrogen Peroxide, Iodine and Iodate Ion", Journal of The American Chemical Society, 1931, vol. 53, No. 01, pp. 38-44.
Bull, "Iron-Ethylenediaminetetraacetic Acid (EDTA)-Catalyzed Superoxide Dismutation Revisited: An Explanation of Why The Dismutase Activity of Fe-EDTA Cannot Be Detected in The Cytochrome c/Xanthine Oxidase Assay System", Archives of Biochemistry and Biophysics, 1982, vol. 215, No. 02, pp. 551-555, XP024804756.
Chen, "Dual Enzyme-like Activities of Iron Oxide Nanoparticles and Their Implication for Diminishing Cytotoxicity", ACS Nano, 2012, vol. 06, No. 05, pp. 4001-4012.
Day, "Catalase and Glutathione Peroxidase Mimics", Biochemical Pharmacology, 2009, vol. 77, No. 03, pp. 285-296.
Gao, "Nanocatalysts Promote Streptococcus Mutans Biofilm Matrix Degradation and Enhance Bacterial Killing to Suppress Dental Caries in Vivo", Biomaterials, 2016, vol. 101, pp. 272-284.
Koo, "A New Cost Effective Approach for Plaque Control and Tooth Decay Prevention", Penn Center for Innovation, [retrieved from the internet on Jun. 12, 2019], URL < http://upenn.technologypublisher.com/technology/22598 >, p. 1.
Kraus et al., "Salivary Catalase and Peroxidase values in Normal Subjects and in Persons with Periodontal Disease." O.S, O.M, & O.P. Jan. 1958; vol. 11, No. 1; pp. 95-102 (Year: 1958).
Livingston, "The Catalytic Decomposition of Hydrogen Peroxide In An Acid Chlorine-Chloride Solution", Journal of the American Chemical Society, 1925, vol. 47, No. 08, pp. 2069-2082.
Nardello, "Identification of the Precursor of Singlet Oxygen ($^1O_2$, $^1\Delta_g$) Involved in The Disproportionation of Hydrogen Peroxide Catalyzed by Calcium Hydroxide", Chemical Communications, 1998, vol. 05, pp. 599-600.
Nardello, "Inorganic Compounds and Materials As Catalysts for Oxidations With Aqueous Hydrogen Peroxide", Journal of Molecular Catalysis. A Chemical, 2006, vol. 251, No. 1-2, pp. 185-193, XP028015283.
Rauen, "Conversion of the Synthetic Catalase Mimic Precursor TAA-1 into the Active Catalase Mimic in Isolated Hepatocytes", Chemical Biology and Drug Design, 2009, vol. 73, No. 05, pp. 494-501.
Signorella, "Bioinspired Functional Mimics of the Manganese Catalases", Coordination Chemistry Reviews, 2012, vol. 256, No. 11-12, pp. 1229-1245.
Tovmasyan, "A Comprehensive Evaluation of Catalase-Like Activity of Different Classes of Redox-Active Therapeutics", Free Radical Biology and Medicine, 2015, vol. 86, pp. 308-321.
Wahlen, "Disproportionation of Hydrogen Peroxide Into Singlet Oxygen Catalyzed by Lanthanum-Exchanged Zeolites", Journal of Catalysis, 2005, vol. 233, No. 02, pp. 422- 433.
Wahlen, "Lanthanum-Doped Zinc Hydroxycarbonates for the Catalytic Disproportionation of Hydrogen Peroxide Into Singlet Oxygen", Journal of Catalysis, 2007, vol. 249, No. 01, pp. 15-23.
Walling, "The Iron(III)-Ethylenediaminetetraacetic Acid-Peroxide System", Inorganic Chemistry, 1970, vol. 09, No. 04, pp. 931-937.
Wu, "Structural, Spectroscopic, and Reactivity Models for the Manganese Catalases", Chemical Reviews, 2004, vol. 104, No. 02, pp. 903-938.

\* cited by examiner

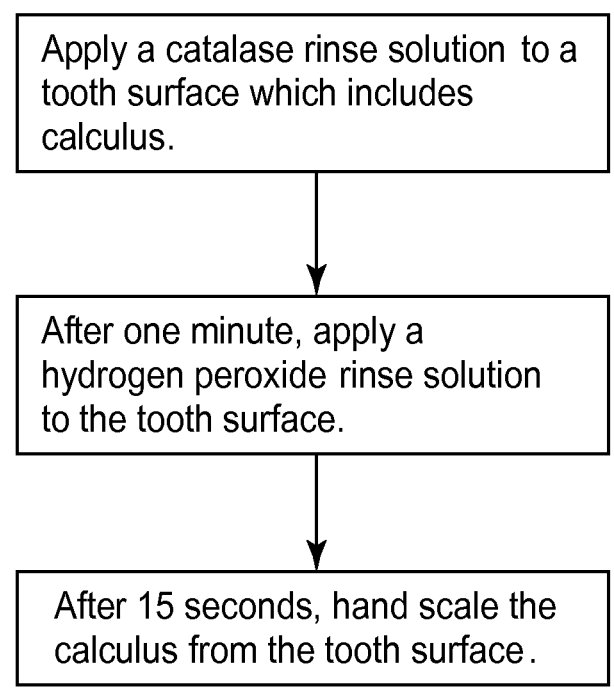

METHODS AND KITS OF REMOVING CALCULUS

BACKGROUND

Dental calculus may lead to periodontal diseases including gingivitis and periodontitis. The existing methods of removing dental calculus rely upon mechanical means such as scaling by trained dental professionals. Such existing removal procedures can be painful and uncomfortable for patients. In addition, the existing removal procedures can put a significant physical burden on the hygienist, often times leading to muscular and repetitive movement ailments (e.g., carpal tunnel syndrome). Moreover, a significant amount of time during the dental prophylaxis procedure is allocated to calculus removal. It is therefore desirable to create a better solution to remove calculus.

SUMMARY

Some aspects of the present disclosure provide a method of removing calculus from a tooth. The method can include applying a component A to the tooth, wherein the component A comprises a hydrogen peroxide or a precursor thereto; applying a component B to the tooth, thereby generating oxygen, wherein the component B comprises a catalase; and removing at least a part of the calculus from the tooth; wherein the component A is applied before or after the component B is applied.

Some aspects of the present disclosure provide a kit of parts for removing calculus from a tooth. The kit can include a component A comprising a hydrogen peroxide or a precursor thereto and a component B comprising a catalase; wherein the component A is applied to the tooth before or after the component B is applied to the tooth.

BRIEF DESCRIPTION OF THE DRAWING

FIG. 1 is a block diagram illustrating the steps of present disclosure for removing calculus from a tooth according to one embodiment of the present disclosure.

DETAILED DESCRIPTION

Before any embodiments of the present disclosure are explained in detail, it is understood that the invention is not limited in its application to the details of use, construction, and the arrangement of components set forth in the following description. The invention is capable of other embodiments and of being practiced or of being carried out in various ways that will become apparent to a person of ordinary skill in the art upon reading the present disclosure. Also, it is understood that the phraseology and terminology used herein is for the purpose of description and should not be regarded as limiting. The use of "including," "comprising," or "having" and variations thereof herein is meant to encompass the items listed thereafter and equivalents thereof as well as additional items. It is understood that other embodiments may be utilized and structural or logical changes may be made without departing from the scope of the present disclosure.

Dental calculus (also referred to as dental tartar) is defined as mineralized dental biofilm filled with crystals of various calcium phosphates or dental plaque that has partially or completely calcified. It may be caused by the continual accumulation of minerals from fluids in the oral environment on plaque on the teeth. Dental calculus is a common oral condition afflicting humans and a variety of animal species and the presence of dental calculus may lead to periodontal diseases. The existing methods of removing dental calculus, which rely upon mechanical means such as scaling, are time consuming and laborious for dental professionals, and can be a painful and unpleasant experience for patients.

The present disclosure generally relates to methods and kits of removing calculus from a tooth. Generally, the method can include applying a component A comprising a hydrogen peroxide or a hydrogen peroxide precursor to the tooth; applying a component B comprising a catalase to the tooth, thereby generating oxygen; and removing at least a part of the calculus from the tooth. The method of the present disclosure can, for example provide an easier removal of dental calculus. In addition, the method of the present disclosure can reduce the time of calculus removal. For example, after the application of the component A and component B, removing the calculus is easier and quicker. Thus, the method of the present disclosure can enable improved procedural efficiency, opportunities for more patients, additional time for other procedures and increased rest periods for the dental professional.

In some embodiments, the component A can include hydrogen peroxide. The hydrogen peroxide can be generated by a peroxide generating enzyme in combination with the corresponding substrate, e.g., glucose oxidase and Superoxide Dismutase (SOD). For example, glucose oxidase can catalyze the oxidation of glucose to hydrogen peroxide. In some embodiments, the hydrogen peroxide may be in a form of a hydrogen peroxide adduct, such as carbamide peroxide, percarbonate salts or acids and polyvinylpyrrolidone (PVP) peroxide. Suitable percarbonate salts or acids can include, but are not limited to percarbonic acid, sodium percarbonate, potassium percarbonate, magnesium percarbonate, calcium percarbonate, zinc percarbonate.

In some embodiments, the component A can include a hydrogen peroxide precursor, such as perborate salts or acids, metal peroxides, organic peroxide, inorganic peroxyacids or salts and combinations thereof. Suitable perborate salts or acids can include, but are not limited to perboric acid, sodium perborate, potassium perborate, magnesium perborate, calcium perborate, and zinc perborate. Suitable metal peroxides can include, but are not limited to calcium peroxide and magnesium peroxide. Suitable organic peroxides can include, but are not limited to peroxycarboxylic acids, such as peracetic acid or salts thereof, permalonic acid or salts thereof, pertartaric acid or salts thereof and percitric acid or salts thereof. In some embodiments, the organic peroxide can be a peracetate salt. Suitable inorganic peroxyacids or salts can include, but are not limited to peroxymonosulfuric acid, peroxyphosphoric acid and a potassium salt of a sulfuric peroxyacid.

In some embodiments, the component A can include at least about 0.003 M hydrogen peroxide. In some of these embodiments, the component A can include from about 0.03 M to about 12 M hydrogen peroxide. In some of these embodiments, the component A can include from about 0.03 M to about 3 M hydrogen peroxide. In some embodiments, the component A can include hydrogen peroxide in an amount of about 0.01 wt %, about 0.1 wt %, about 1 wt %, about 5 wt %, about 10 wt %, about 30 wt %, about 35 wt %, or a range between and including any two of these values. In other embodiments, the component A can comprise a hydrogen peroxide precursor or hydrogen peroxide adduct capable of producing a similar concentration of hydrogen peroxide, for example, at least about 0.003 M hydrogen peroxide. For instance, a 15 wt % carbamide peroxide solution can produce a solution which includes about 5 wt % hydrogen peroxide.

In some embodiments, the component B can include a peroxidase. In some embodiments, the component B can include a catalase. Catalases can be found in a wide variety of eukaryotic and prokaryotic organisms including, but not limited to *Agrobacterium tumefaciens, Aliivibrio salmonicida, Anopheles gambiae, Aspergillus nidulans*, and *Aspergillus niger*. Suitable catalases that can be used in the present disclosure are well known in the art and can include those described in International Publication No. WO2012/072777. For example, suitable catalases can include catalase derived/isolated from bovine liver, *Aspergillus niger* and *Micrococcus lysodeikticus*. In some embodiments, catalase can be in an unisolated form, such as a part of or whole eukaryotic and prokaryotic organism. Catalases can catalyze the disproportionation of two molecules of hydrogen peroxide into two molecules water and one molecule oxygen.

In some embodiments, the component B can include greater than about 3 units/mL of catalase. In some embodiments, the component B can include greater than about 17 units/mL of catalase. As used herein, one unit catalase will decompose 1.0 μmole of hydrogen peroxide per minute at pH 7.0 at 25° C., while the hydrogen peroxide concentration falls from 10.3 to 9.2 mM, measured by the rate of decrease of $A_{240}$. In some of these embodiments, the component B can include catalase in an amount of about 30 units/mL, about 300 units/mL, about 3,000 units/mL, about 30,000 units/mL, about 300,000 units/mL, or a range between and including any two of these values, for example from about 30 units/mL to about 3,000 units/mL. In some of these embodiments, after the component B is applied to the tooth surface, the concentration of catalase inside the oral cavity increases by at least about 5 units/mL, about 10 units/mL, about 20 units/mL, about 30 units/mL, about 100 units/mL, about 300 units/mL, about 3,000 units/mL, about 30,000 units/mL, or a range between and including any two of these values, above the natural concentration of catalase present inside the oral cavity prior to application of the component B.

Generally, the component A is applied to the tooth surface before or after the component B is applied to the tooth surface. In some embodiments, the component A is applied at least 30 seconds before or after the component B is applied. Either component A or component B can be (independently) in any form suitable for oral cavity delivery, such as in the form of aqueous solutions (e.g., a rinse), a gel, a paste, or a powder. For example, component A and component B can be applied both as rinses. In some embodiments, component A can be applied as a gel and component B can be applied as a rinse.

In some embodiments, methods of the present disclosure include relatively short exposure times of component A, such that no noticeable bleaching is observed by the naked eye when the method is performed, e.g., in a single instance, and in some cases, over multiple instances.

In some embodiments, the component A or component B is applied for a period less than about 1 hour, less than about 30 minutes, less than about 10 minutes, less than about 5 minutes, less than about 2 minutes, or less than about 1 minute. In some of these embodiments, the component A or component B is applied for about 10 minutes, about 5 minutes, about 2 minutes, about 1 minute, about 30 seconds, about 15 seconds or a range between and including any two of these values. In some embodiments, both the component A and the component B are each applied for a period less than about 1 hour, less than about 30 minutes, less than about 10 minutes, less than about 5 minutes, less than about 2 minutes, or less than about 1 minute.

As the hydrogen peroxide adduct or hydrogen peroxide precursor is applied to the tooth, it dissociates in the environment within the oral cavity to produce hydrogen peroxide. In some embodiments, hydrogen peroxide in the presence of peroxidase, e.g., catalase can cause release of oxygen, thereby loosening the calculus from the tooth. The generated oxygen can, for example weaken the adhesion between the calculus and tooth surface so that the calculus can be removed easily after relatively short exposure times to Component A and Component B. In some embodiments, the generated oxygen can soften and/or loosen the calculus so that the removal of the calculus, for example, by hand scaling is much easier. For instance, the calculus can be removed in a shorter time or with a less force. The catalase concentration typically present in human saliva or oral cavity is not sufficient to provide these effects.

After the component A and the component B are applied, at least a part of the calculus can be removed from the tooth by any suitable mechanical means, e.g., scaling (such as using a dental scaler), brushing, swabbing, wiping, ultrasonic, air polishing or jetted water. In some embodiments, the part of the calculus may be removed by mechanical means other than toothbrushing, for example by a dental scaler. In some embodiments, removing step occurs within 1 day, 12 hours, 6 hours, 3 hours, 1 hour, 30 minutes, 10 minutes, 5 minutes, 2 minutes, 1 minute, 30 seconds, or 15 seconds after the applying steps. In some embodiments, removing step lasts for a period less than about 10 minutes, less than about 5 minutes, less than about 2 minutes, or less than about 1 minute. In other embodiments, removing step lasts about 10 minutes, about 5 minutes, about 2 minutes, about 1 minute, about 30 seconds, or a range between and including any two of these values. Thus, the method of the present disclosure can, for example, provide an easier and/or quicker removal of the calculus. In some embodiments, the applying steps and removing step are all completed in less than about 1 day, about 12 hours, about 6 hours, about 3 hours, about 1 hour, about 30 minutes, about 10 minutes, about 5 minutes, about 2 minutes, or about 1 minute.

The flow chart in FIG. 1 depicts an exemplified method according to one embodiment of the present disclosure. As shown in FIG. 1, first a catalase rinse solution is applied to a tooth surface which includes calculus. After one minute, a hydrogen peroxide aqueous rinse solution is applied to the tooth surface. After about 15 seconds, calculus is hand scaled.

In some embodiments, additives can be applied to the tooth surface. In some of these embodiments, additives can be applied with the component A and/or the component B. The additives used in the method can include, but are not limited to, antiseptics and preservatives, antibiotics, flavoring materials, surfactants, abrasives, thickeners and binders, propellants, carriers, tartar control agents, calcium sequestrants, fluoride salts, and dyes.

Suitable antiseptics and preservatives can include, but are not limited to, chlorhexidine and salts thereof, polyhexamethylene biguanide, octenidine, quaternary ammonium salts and polymers thereof, organic acids, chelating agents for example a calcium chelating agent (e.g., Ethylenediaminetetraacetic acid (EDTA)), essential oils, and parabens. Examples of antiseptics and preservatives can include those described in U.S. Pat. No. 8,647,608. Non-limiting examples of antibiotics can include penicillin, tetracycline, minocycline, and the like. Examples of antibiotics can also include those described in U.S. Pat. No. 6,685,921. Examples of flavoring materials can include artificial sweeteners, plant oils, and synthetic flavors. Examples of abrasives can include silica particles, synthetic inorganic particles, and synthetic or plant derived organic particles. Suitable surfactants can include those described in U.S. Publication No. 2006/0051385. Examples of such surfactants include cationic surfactants, zwitterionic surfactants, non-ionic surfactants and anionic surfactants. Examples of thickeners can include glycerol, silica, cellulose-based polymers, plant gums (e.g. guar and xanthan gum), petroleum derived materials such as petrolatum, polyethylene glycols, polyvinyl pyrrolidone and co-polymers thereof, polylactic acids, long chain fatty acid alcohols, and acrylate polymers. Suitable binders can include those described in U.S. Pat. No. 8,647,608. Suitable carriers can include those described in U.S. Pat. No. 8,647,608. Carriers can include any alcohols suitable for use in a subject's oral cavity, including ethanol and isopropanol and glycerol. Suitable dyes include those described in U.S. Pat. No. 8,647,608. Examples of tartar control agents include those described in U.S. Pat. No. 6,685,921. Anti-tartar agents known for use in dental care products can include, but are not limited to phosphate. Phosphates can include pyrophosphates, polyphosphates, polyphosphonates and mixtures thereof. Pyrophosphate salts can include the dialkali metal pyrophosphate salts, tetra-alkali metal pyrophosphate salts and mixtures thereof. Examples of fluoride salts can include those described in U.S. Pat. Nos. 6,685,921, 3,535,421 and 3,678,154.

The kits of removing calculus from a tooth of the present disclosure can include a component A comprising a hydrogen peroxide or a precursor thereto and a component B comprising a catalase. The component A of the kit is applied to the tooth before or after the component B of the kit is applied to the tooth.

The following embodiments are intended to be illustrative of the present disclosure and not limiting.

EMBODIMENTS

Embodiment 1 is a method of removing calculus from a tooth comprising:
  applying a component A to the tooth, wherein the component A comprises a hydrogen peroxide or a precursor thereto;
  applying a component B to the tooth, thereby generating oxygen, wherein the component B comprises a catalase; and
  removing at least a part of the calculus from the tooth;
  wherein the component A is applied before or after the component B is applied.
Embodiment 2 is the method of embodiment 1, wherein the component A comprises at least about 0.003 M hydrogen peroxide.
Embodiment 3 is the method of embodiment 2, wherein the component A comprises from about 0.03 M to about 12 M hydrogen peroxide.
Embodiment 4 is the method of embodiments 1 to 3, wherein the component B comprises greater than about 3 units/mL of catalase
Embodiment 5 is the method of embodiment 4, wherein the component B comprises from about 30 units/mL to about 300,000 units/mL catalase.
Embodiment 6 is the method of embodiment 5, wherein the component B comprises from about 30 units/mL to about 3,000 units/mL catalase Embodiment 7 is the method of embodiments 1 to 6, wherein the component A is applied for a period less than about 1 hour.
Embodiment 8 is the method of embodiments 1 to 7, wherein the component B is applied for a period of less than about 1 hour.
Embodiment 9 is the method of embodiments 1 to 8, wherein both the component A and the component B are each applied for a period of less than about 1 hour.
Embodiment 10 is the method of embodiments 1 to 9, wherein removing step occurs within 1 day after the applying steps.
Embodiment 11 is the method of embodiments 1 to 10, wherein the applying steps and removing step are all completed in less than about 1 day.
Embodiment 12 is the method of embodiments 1 to 11, wherein the hydrogen peroxide is a hydrogen peroxide adduct.
Embodiment 13 is the method of embodiment 12, wherein the hydrogen peroxide adduct is selected from the group consisting of carbamide peroxide, percarbonate salts or acids, polyvinylpyrrolidone (PVP) peroxide and combinations thereof.
Embodiment 14 is the method of embodiment 13, wherein the hydrogen peroxide adduct is carbamide peroxide.
Embodiment 15 is the method of embodiments 1 to 11, wherein the hydrogen peroxide precursor is selected from the group consisting of perborate salts or acids, metal peroxides, organic peroxide, inorganic peroxyacids or salts and combinations thereof.
Embodiment 16 is the method of embodiment 15, wherein the precursor is a perborate salt or acid.
Embodiment 17 is the method of embodiment 15, wherein the precursor is an organic peroxide.
Embodiment 18 is the method of embodiment 17, wherein the organic peroxide is a peracetate salt or acid.
Embodiment 19 is the method of embodiments 1 to 11, wherein the hydrogen peroxide is generated by a peroxide generating enzyme.
Embodiment 20 is the method of embodiment 19, wherein the peroxide generating enzyme is glucose oxidase.
Embodiment 21 is the method of embodiments 1 to 20, wherein the part of the calculus is removed by mechanical means.
Embodiment 22 is the method of embodiment 21, wherein the part of the calculus is removed by mechanical means other than toothbrushing.
Embodiment 23 is the method of embodiment 22, wherein the part of the calculus is removed by a dental scaler.
Embodiment 24 is a kit of parts for removing calculus from a tooth comprising:
  a component A comprising a hydrogen peroxide or a precursor thereto; and
  a component B comprising a catalase;
  wherein the component A is applied to the tooth before or after the component B is applied to the tooth.

EXAMPLES

The following examples are given to illustrate, but not limit, the scope of this invention. As used herein, all parts and percentages are by weight unless otherwise specified. All commercial materials were used as obtained from the vendor. Unless otherwise specified, materials can be obtained from Sigma-Aldrich Corp. (St. Louis, Mo.).

Materials & Methods

Bovine liver, *Aspergillus niger* catalase enzymes, glycerol, phosphate buffered saline, and potassium hydroxide, as further detailed below, were obtained from Sigma-Aldrich Corp (unless otherwise specified below).

Hydrogen peroxide ($H_2O_2$), in the form of 30 or 35 wt. % aqueous solutions, was obtained from Sigma-Aldrich, Avantor Performance Materials (Center Valley, Pa.), or Acros (Geel, Belgium). Diluted aqueous hydrogen peroxide solutions were prepared using either deionized or distilled water. The molarity of the aqueous hydrogen peroxide solutions at room temperature (~23° C.) was calculated from the weight percent and approximate density of the solutions (densities were calculated at 25° C. using Equation (3) in Easton, M. F., Mitchell, A. G., Wynne-Jones, W. F. K., "The Behaviour of Mixtures of Hydrogen Peroxide and Water. Part I. Determination of the Densities of Mixtures of Hydrogen Peroxide and Water", Trans. Faraday Soc., 48, 796 (1952)).

Carbamide peroxide (also referred to as "urea hydrogen peroxide" or "UHP") was obtained from Johnson Matthey, Alfa Aesar Division (Ward Hill, Mass.).

Carbopol 971, was obtained from Lubrizol Corporation (Wickliffe, Ohio).

Extracted human teeth containing multiple regions with calculus deposits (available from various suppliers such as enretec GmbH, Velten, Germany) and stored in 0.5-1.0 wt. % aqueous chloramine-T solution prior to use. To prepare the extracted teeth for calculus removal testing, the teeth were rinsed with distilled water and dried with compressed air. Hand scaling of calculus deposits as described in the following examples was performed using a universal (i.e., Columbia) curette commercially available from either OSUNG MND CO., LTD. (Korea) or Hu-Friedy (Netherlands).

Example 1: *Aspergillus niger* Catalase (40 U/mL)+10 wt. % (~3 M) Hydrogen Peroxide Two separate regions of calculus deposits on a single tooth were hand scaled following the application of either a control buffer solution or the treatment formulation to each region. The effectiveness of the formulation was determined by comparing the ease of calculus removal by hand scaling after application of the control buffer solution in the first region of calculus versus application of the treatment formulation in the second region of calculus.

A solution containing 40 U/mL catalase (*Aspergillus niger*, obtained from the supplier with an activity of 207,390 U/mL) in 50 mM potassium phosphate ($K_2HPO_4.3H_2O$) buffer was prepared. 50 mM potassium phosphate was used as a control buffer solution. On one region of calculus deposit, 15 µL of control buffer solution was applied to the calculus, followed one minute later by hand scaling for 30-60 seconds. The treatment formulation was applied to a different region of calculus by first applying 15 µL of the catalase solution, followed one minute later by the addition of 15 µL of 10 wt. % hydrogen peroxide aqueous solution. After approximately 15 seconds, hand scaling was initiated and performed for 30-60 seconds. A noticeable improvement in the ease of calculus removal by hand scaling was observed after using the treatment formulation when compared with the control buffer solution.

Example 2: Bovine Liver Catalase (67,120 U/mL)+35 wt. % (~12 M) Aqueous Hydrogen Peroxide Two separate regions of calculus deposits on a single tooth were hand scaled on the untreated region of calculus (control) or following the application of the treatment formulation to another region. The effectiveness of the formulation was determined by comparing the ease of calculus removal by hand scaling on one control region versus application of the treatment formulation in a different region of calculus.

As a control, the ease of removal without treatment was determined by removal of calculus by hand scaling of one region of the calculus. The treatment formulation was applied to a different region of calculus by first applying 40 µL of an aqueous solution (67,120 U/mL) of catalase (bovine liver, obtained from the supplier with an activity of 3,356 U/mg), followed two minutes later by the addition of approximately 40 µL of 35 wt. % hydrogen peroxide aqueous solution. After an additional two minutes, the treated calculus was removed by hand scaling for 30-60 seconds. A noticeable improvement in the ease of calculus removal by hand scaling was observed after using the treatment formulation when compared with the control (i.e., no treatment).

Example 3: Bovine Liver Catalase (300,000 U/mL)+0.1 wt. % (~0.03 M) Aqueous Hydrogen Peroxide Two separate regions of calculus deposits on a single tooth were hand scaled following the application of either deionized water or the treatment formulation to each region. The effectiveness of the formulation was determined by comparing the ease of calculus removal by hand scaling after application of deionized water in one region of calculus versus application of the treatment formulation in a different region of calculus.

An aqueous catalase solution was prepared by dissolving and dispersing catalase (bovine liver, obtained from the supplier with an activity of 3,187 U/mg) into sufficient deionized water to reach a concentration of 300,000 U/mL. On one region of calculus deposit, approximately 0.1-0.2 mL of deionized water was used to thoroughly wet the calculus, followed 5 seconds later by hand scaling for 30-60 seconds. The treatment formulation was applied to a different region of calculus by first applying approximately 0.1-0.2 mL of catalase solution to thoroughly wet the calculus, followed 30 seconds later by the addition of 0.1-0.2 mL of 0.1 wt. % hydrogen peroxide aqueous solution. Hand scaling for 30-60 seconds was initiated within 15 seconds after the addition of the aqueous hydrogen peroxide. A noticeable improvement in the ease of calculus removal by hand scaling was observed after using the treatment formulation when compared with the control (i.e., deionized water).

Example 4: Bovine Liver Catalase (3,000 U/mL)+9 wt. % (~1 M) Aqueous Carbamide Peroxide Two separate regions of calculus deposits on a single tooth were hand scaled following the application of either deionized water or the treatment formulation to these regions. The effectiveness of the formulation was determined by comparing the ease of calculus removal by hand scaling after application of deionized water in one region of calculus versus application of the treatment formulation in a different region of calculus.

An aqueous catalase solution was prepared by dissolving and dispersing the catalase (bovine liver, obtained from the supplier with an activity of 3,187 U/mg) into sufficient deionized water to reach a concentration of 3,000 U/mL. On one region of calculus deposit, approximately 0.1-0.2 mL of deionized water was used to thoroughly wet the calculus, followed 5 seconds later by hand scaling for 30-60 seconds. The treatment formulation was applied to a different region of calculus by first applying approximately 0.1-0.2 mL of catalase solution to thoroughly wet the calculus, followed 30 seconds later by the addition of 0.1-0.2 mL of 9 wt. % aqueous carbamide peroxide solution. Hand scaling for 30-60 seconds was initiated within 15 seconds after the addition of the aqueous carbamide peroxide. A noticeable improvement in the ease of calculus removal by hand scaling was observed after using the treatment formulation when compared with the control (i.e., deionized water).

Example 5: *Aspergillus niger* Catalase (3,000 U/Ml) Gel+3 wt. % (~1 M) Hydrogen Peroxide Gel A 3 wt. % hydrogen peroxide gel was made by diluting a hydrogen peroxide aqueous solution into deionized water, adding Carbopol 971 to a final concentration of 0.52 wt. %, and adding potassium hydroxide to a final concentration of 0.43 wt. %.

A catalase gel containing 3,000 U/ml of *Aspergillus niger* catalase was made by adding *Aspergillus niger* catalase, obtained from American Laboratories (Omaha, Nebr.), to a gel containing final concentrations of 93.83 wt. % of glycerol, 5.41 wt. % of phosphate buffered saline, 0.27 wt. % of Carbopol 971, and 0.22 wt. % of potassium hydroxide.

Twelve dental hygienists, licensed to practice in the United States or Canada, were asked to evaluate the effectiveness of sequentially applied gel formulations on twenty-two human teeth covered in calculus. Half of the calculus on each tooth was scaled by a hygienist after treatment with deionized water. A syringe with a blunted needle tip was then used to apply about 50 microliters of the catalase-containing gel to the calculus on each tooth. About 50 microliters of the hydrogen-peroxide-containing gel was then applied to the same region of calculus on each tooth. The treated region of the calculus was immediately scaled after application of a treatment by the same hygienist who scaled the water-treated region on the same tooth. After scaling, the hygienists were asked to rank their level of satisfaction of the effectiveness with which the treatment helped to remove calculus. The hygienists were provided with a ranking scale of 1 to 7 with 1 being the ranking for very dissatisfied and 7 being the ranking for very satisfied. The hygienists ranked the sequentially applied gel formulations as highly satisfying for improving ease of removal of calculus, with a score 5 or above for 16 of 22 teeth (~73%).

Comparative Example 1: Bovine Liver Catalase (3 U/mL)+5 wt. % (~1.5 M) Aqueous Hydrogen Peroxide Two separate regions of calculus deposits on a single tooth were hand scaled following the application of either deionized water or the treatment formulation to these regions. The effectiveness of the formulation was determined by comparing the ease of calculus removal by hand scaling after application of deionized water in one region of calculus versus application of the treatment formulation in a different region of calculus.

An aqueous catalase solution was prepared by dissolving and dispersing catalase (bovine liver, obtained from the supplier with an activity of 3,187 U/mg) into deionized water to reach a final concentration of 3 U/mL. On one region of calculus deposit, approximately 0.1-0.2 mL of deionized water was used to thoroughly wet the calculus, followed 5 seconds later by hand scaling for 30-60 seconds. The treatment formulation was applied to a different region of calculus by first applying approximately 0.1-0.2 mL of catalase solution to thoroughly wet the calculus, followed 30 seconds later by the addition of 0.1-0.2 mL of 5 wt. % hydrogen peroxide aqueous solution. Hand scaling for 30-60 seconds was initiated within 15 seconds after the addition of the aqueous hydrogen peroxide. No noticeable improvement in the ease of calculus removal by hand scaling was observed after using the treatment formulation when compared with the control (i.e., deionized water).

Comparative Example 2: Bovine Liver Catalase (300,000 U/mL)+0.01 wt. % (~0.003 M) Aqueous Hydrogen Peroxide Two separate regions of calculus deposits on a single tooth were hand scaled following the application of either deionized water or the treatment formulation to these regions. The effectiveness of the formulation was determined by comparing the ease of calculus removal by hand scaling after application of deionized water in one region of calculus versus application of the treatment formulation in a different region of calculus.

An aqueous catalase solution was prepared by dissolving and dispersing catalase (bovine liver, obtained from the supplier with an activity of 3,187 U/mg) into sufficient deionized water to reach a concentration of 300,000 U/mL. On one region of calculus deposit, approximately 0.1-0.2 mL of deionized water was used to thoroughly wet the calculus, followed 5 seconds later by hand scaling for 30-60 seconds. The treatment formulation was applied to a different region of calculus by first applying approximately 0.1-0.2 mL of catalase solution to thoroughly wet the calculus, followed 30 seconds later by the addition of 0.1-0.2 mL of 0.01 wt. % hydrogen peroxide aqueous solution. Hand scaling for 30-60 seconds was initiated within 15 seconds after the addition of the aqueous hydrogen peroxide. No noticeable improvement in the ease of calculus removal by hand scaling was observed after using the treatment formulation when compared with the control (i.e., deionized water).

Comparative Example 3: 30 wt. % (~9.8 M) Aqueous Hydrogen Peroxide

Two separate regions of calculus deposits on a single tooth were hand scaled following the application of either deionized water or the treatment formulation to these regions. The effectiveness of the formulation was determined by comparing the ease of calculus removal by hand scaling after application of deionized water in one region of calculus versus application of the treatment formulation in a different region of calculus.

On one region of calculus deposit, approximately 0.1-0.2 mL of deionized water was used to thoroughly wet the calculus, followed 5 seconds later by hand scaling for 30-60 seconds. The treatment formulation of 30 wt. % hydrogen peroxide aqueous solution was applied to a different region of calculus by applying approximately 0.1-0.2 mL of the hydrogen peroxide solution to thoroughly wet the calculus. Hand scaling for 30-60 seconds was initiated within 15 seconds after the addition of the aqueous hydrogen peroxide. No noticeable improvement in the ease of calculus removal by hand scaling was observed after using the treatment formulation when compared with the control (i.e., deionized water).

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

The complete disclosures of the patents, patent documents, and publications cited herein are incorporated by reference in their entirety as if each were individually incorporated.

What is claimed is:

1. A method of removing calculus from a tooth comprising:
    applying a component A to the tooth surface, wherein the component A comprises at least 0.1 wt-% hydrogen peroxide or a precursor thereto providing at least 0.1 wt-% hydrogen peroxide;
    applying a component B to the tooth surface, thereby generating oxygen, wherein the component B comprises at least 30 units/mL catalase; and
    removing at least a part of the calculus from the tooth surface;
    wherein the component A is applied to the tooth surface before or after the component B is applied to the tooth surface;
    wherein after the component B is applied to the tooth surface, the concentration of catalase inside the oral cavity increases above the natural concentration of catalase present inside the oral cavity prior to the application of the component B.

2. The method of claim 1, wherein the component A comprises at least 1 wt-% or a precursor thereto providing at least 1 wt-% hydrogen peroxide.

3. The method of claim 1, wherein the component B comprises at least 300 units/mL catalase.

4. The method of claim 3, wherein the component B comprises 300 units/mL to 300,000 units/mL catalase.

5. The method of claim 1, wherein the component A is applied for a period less than about 1 hour.

6. The method of claim 1, wherein the component B is applied for a period of less than about 1 hour.

7. The method of claim 1, wherein the component A is applied to the tooth surface at least 30 seconds before or after the component B is applied to the tooth surface.

8. The method of claim 1, wherein removing step occurs within 1 day after the applying steps.

9. The method of claim 1, wherein the applying steps and removing step are all completed in less than about 1 day.

10. The method of claim 1, wherein the hydrogen peroxide is a hydrogen peroxide adduct.

11. The method of claim 10, wherein the hydrogen peroxide adduct is selected from the group consisting of carbamide peroxide, percarbonate salts or acids, polyvinylpyrrolidone (PVP) peroxide and combinations thereof.

12. The method of claim 1, wherein the hydrogen peroxide precursor is selected from the group consisting of perborate salts or acids, metal peroxides, organic peroxide, inorganic peroxyacids or salts and combinations thereof.

13. The method of claim 12, wherein the precursor is an organic peroxide, and wherein the organic peroxide is a peracetate salt or acid.

14. The method of claim 1, wherein the hydrogen peroxide is generated by a peroxide generating enzyme.

15. The method of claim 1, wherein the at least a part of the calculus is removed by mechanical means.

16. The method of claim 15, wherein the at least a part of the calculus is removed by mechanical means other than toothbrushing.

17. The method of claim 16, wherein the at least a part of the calculus is removed by a dental scaler.

18. The method of claim 1, wherein the component A comprises at least 0.1 wt-% to 35 wt-% hydrogen peroxide or a precursor thereto providing 0.1 wt-% to 35 wt-% hydrogen peroxide.

19. The method of claim 2, wherein the component A comprises 1 wt-% to 30 wt-% hydrogen peroxide or a precursor thereto providing 1 wt-% to 30 wt-% hydrogen peroxide.

20. The method of claim 19, wherein the component A comprises 1 wt-% to 10 wt-% hydrogen peroxide or a precursor thereto providing 1 wt-% to 10 wt-% hydrogen peroxide.

21. The method of claim 1, wherein the component B comprises 30 units/mL to 300,000 units/mL catalase.

22. The method of claim 4, wherein the component B comprises 300 units/mL to 30,000 units/mL catalase.

23. A method of removing calculus from a tooth comprising:
    applying a component A to the tooth surface, wherein the component A comprises 1 wt-% to 10 wt-% hydrogen peroxide or a precursor thereto providing 1 to 10 wt-% wt-% hydrogen peroxide;
    applying a component B to the tooth surface, thereby generating oxygen, wherein the component B comprises at least 300 units/mL to 30,000 units/mL catalase; and
    removing at least a part of the calculus from the tooth surface;
    wherein the component A is applied to the tooth surface before or after the component B is applied to the tooth surface;
    wherein after the component B is applied to the tooth surface, the concentration of catalase inside the oral cavity increases above the natural concentration of catalase present inside the oral cavity prior to the application of the component B.

* * * * *